US009031633B2

(12) United States Patent
Rahmer et al.

(10) Patent No.: US 9,031,633 B2
(45) Date of Patent: *May 12, 2015

(54) ARRANGEMENT AND METHOD FOR DETECTING AND/OR LOCATING A MAGNETIC MATERIAL IN A REGION OF ACTION

(75) Inventors: Juergen Erwin Rahmer, Hamburg (DE); Jeurgen Weizenecker, Stutensee (DE); Bernhard Gleich, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 653 days.

This patent is subject to a terminal disclaimer.

(21) Appl. No.: 13/132,322

(22) PCT Filed: Dec. 2, 2009

(86) PCT No.: PCT/IB2009/055455
§ 371 (c)(1),
(2), (4) Date: Jun. 2, 2011

(87) PCT Pub. No.: WO2010/067264
PCT Pub. Date: Jun. 17, 2010

(65) Prior Publication Data
US 2011/0246103 A1 Oct. 6, 2011

(30) Foreign Application Priority Data
Dec. 8, 2008 (EP) .................................. 08170920

(51) Int. Cl.
*A61B 5/05* (2006.01)
*G01R 33/12* (2006.01)
*G01N 27/72* (2006.01)

(52) U.S. Cl.
CPC ................. *A61B 5/05* (2013.01); *A61B 5/0515* (2013.01)

(58) Field of Classification Search
USPC .......... 600/407, 420, 409, 422–425; 328/204, 328/228, 307, 309, 318; 607/105; 73/53.01; 702/57; 324/204, 228, 307, 309, 318
See application file for complete search history.

(56) References Cited

U.S. PATENT DOCUMENTS

| 2003/0085703 | A1 | 5/2003 | Gleich | |
|---|---|---|---|---|
| 2009/0240135 | A1* | 9/2009 | Gleich et al. .................. | 600/409 |
| 2011/0089942 | A1* | 4/2011 | Goodwill et al. ............. | 324/301 |
| 2011/0246103 | A1 | 10/2011 | Rahmer et al. | |

FOREIGN PATENT DOCUMENTS

| WO | 2006064392 A2 | 6/2006 |
|---|---|---|
| WO | 2006064405 A1 | 6/2006 |

OTHER PUBLICATIONS

By T.Knopp et al: "Singular Value Analys for Magnetic Particle Imaging" Nuclear Science Symposium Conference Record, 2008. NSS '08. IEEE (Oct. 19-25, 2008), IEEE, Piscataway, NJ, USA, XP031418565 ISBN: 978-1-4244-2714-7 the whole document Oct. 19, 2008, pp. 4525-4529.

* cited by examiner

Primary Examiner — Long V Le
Assistant Examiner — Lawrence Laryea

(57) ABSTRACT

In Magnetic Particle Imaging (MPI) the reconstruction requires the knowledge of a so called system function. This function describes the relation between spatial position and frequency response and is currently measured once for a scanner set-up and a tracer material. For reasonable resolutions and fields of view the system function becomes quite large, resulting in large acquisition times to obtain reasonable signal-to-noise. However, the system function has a number of properties which can be used to improve signal-to-noise. According to the present invention use is made of the spatial symmetry and/or identical responses at different frequencies for this purpose.

10 Claims, 16 Drawing Sheets

ARRANGEMENT AND METHOD FOR DETECTING AND/OR LOCATING A MAGNETIC MATERIAL IN A REGION OF ACTION

FIELD OF THE INVENTION

The present invention relates to an arrangement for detecting and/or locating a magnetic material in a region of action. Further, the present invention relates to a processor for use in such an arrangement. Still further, the present invention relates to corresponding methods and to a computer program for control of the arrangement.

BACKGROUND OF THE INVENTION

An arrangement of this kind is known from German patent application DE 101 51 778 A1. In the arrangement described in that publication, first of all a magnetic field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement has the advantage that it can be used to examine arbitrary examination objects—e.g. human bodies—in a non-destructive manner and without causing any damage and with a high spatial resolution, both close to the surface and remote from the surface of the examination object.

A similar arrangement and method is known from Gleich, B. and Weizenecker, J. (2005), "Tomographic imaging using the nonlinear response of magnetic particles" in nature, vol. 435, 30 Jun. 2005, pp. 1214-1217. The arrangement and method for magnetic particle imaging (MPI) described in that publication takes advantage of the non-linear magnetization curve of small magnetic particles.

MPI is a method for imaging distributions of magnetic nano-particles which combines high sensitivity with the ability of fast dynamic imaging, making it a promising candidate for medical imaging applications. MPI applies a new method of signal encoding based on the dynamic displacement of a localized excitation process and allows fast volumetric imaging. However, in contrast to established imaging modalities like MRI and CT, no simple mathematical transform has yet been identified to reconstruct images from the acquired data. Therefore, MPI image reconstruction requires knowledge of a "system function" describing the system response to a given spatial distribution of particles, i.e., mapping particle position to frequency response. To solve the reconstruction problem, the system function has to be inverted, usually requiring some regularization scheme.

The system function can be determined experimentally by measuring the magnetization response of a point-like sample at a large number of spatial positions corresponding to the number of image pixels or voxels. This calibration procedure requires very long acquisition times and furthermore provides a system function that is contaminated with noise. Due to the large size of the system function matrix, solving the inverse reconstruction problem is also quite time-consuming and requires large amounts of computer memory. Also to obtain a reasonable signal-to-noise ratio (SNR) a large acquisition time is required.

SUMMARY OF THE INVENTION

It is an object of the present invention to provide an arrangement and a method for detecting and/or locating a magnetic material in a region of action by which the SNR can be increased. Preferably, the proposed arrangement and method shall also require less time for acquisition of the system function data of the system function and/or for image reconstruction and/or less storage space for storing the system function data of the system function Further, a corresponding processor and processing method as well as a computer program for control of the arrangement shall be provided.

In a first aspect of the present invention an arrangement as defined in claim 1 is presented comprising:
  selection means for generating a magnetic selection field having a pattern in space of its magnetic field strength such that a first sub-zone having a low magnetic field strength and a second sub-zone having a higher magnetic field strength are formed in the region of action,
  drive means for changing the position in space of the two sub-zones in the region of action by means of a magnetic drive field so that the magnetization of the magnetic material changes locally,
  receiving means for acquiring detection signals, which detection signals depend on the magnetization in the region of action, which magnetization is influenced by the change in the position in space of the first and second sub-zone,
  storage means for storing at least a subset of measured system function data of the arrangement's system function, said system function comprising a system function data set describing the relation between spatial position of the magnetic material and the system response for said arrangement and the trajectory along which said first sub-zone is moved for the acquisition of said system function data,
  processing means for generating processed system function data having a higher SNR than said measured system function data by processing said measured system function data using additional knowledge about the structure of the system function, and
  reconstruction means for reconstructing the spatial distribution of the magnetic material in the region of action from the detection signals and said processed system function data.

In a second aspect of the present invention a processor as claimed in claim 7 is presented for use in an arrangement for detecting and/or locating a magnetic material in a region of action as claimed in claim 1, said processor being adapted for generating processed system function data having a higher SNR than measured system function data by processing said measured system function data using additional knowledge about the structure of the system function.

In a further aspect of the present invention corresponding methods are presented as defined in claims 8 and 9.

In still a further aspect of the present invention a computer program is presented comprising program code means for causing a computer to control an arrangement as claimed in claim 1 to carry out the steps of the method as claimed in claim 8 or 9 when said computer program is carried out on the computer.

Preferred embodiments of the invention are defined in the dependent claims. It shall be understood that the claimed method and computer program have similar and/or identical preferred embodiments as the claimed device and as defined in the dependent claims.

From a theoretical understanding of the signal encoding process insight into the structure of the system function has been gained, which can be used to speed up the system function acquisition and/or to even simulate parts or all of the system function. Information about the matrix structure can also been used to find more compact system function representations, helping to reduce memory requirements and speed up reconstruction. Still further, identification of a mathematical transform leading from the data to the image can be used to speed up the reconstruction process. Finally, knowledge about the properties of the system function has been used to increase the SNR.

According to the first aspect of the present invention this general idea is exploited to increase the SNR. In particular, knowledge about the structure of the system function is used in the reconstruction. This knowledge can comprise, as defined in preferred embodiments, simple spatial symmetries occurring in the frequency components of the system function or information about spectral redundancies in the spatial components. This knowledge can be derived from an analytical analysis of the MPI encoding scheme or a simulation of the encoding process, both for a given combination of the arrangement, i.e. scanner setup, trajectory of movement of the first sub-zone having a low magnetic field strength (also referred to as "field free point", FFP), and magnetic material.

According to a preferred embodiment said processing means are adapted for combining, in particular averaging, signals acquired at different spatial positions, which share the same information due to the spatial symmetries, in particular spatial mirror symmetries, existing in the frequency components of the complete system function. Such spatial symmetries can not only be obtained by practical measurements, but also from theoretical considerations using knowledge of the trajectory (and its symmetry), the particle magnetization curve and the setup of the arrangement (and its symmetry), in particular of its selection means, drive means and receiving means. For instance for a Lissajous trajectory with Langevin particles a spatial mirror symmetry is observed which has a well defined frequency dependent parity. Due to the symmetry identical information exists in the complete system function at different spatial positions, which is combined, for instance averaged, to increase the SNR of the system function.

According to another embodiment said processing means are adapted for summing up frequency components of the complete system function data with similar spatial information. As multiple drive field frequencies are involved in the field free point movement the signal generated by the non-linear particle response contains sums and differences of these frequencies. The respective frequency components share the same spatial pattern and can therefore be combined without loss of information. This results in a reduced number of rows in the system function matrix, Preferably, said receiving means are adapted for acquiring the complete system function data of the arrangement's system function by detecting signals while a probe of said magnetic material is subsequently placed at a plurality of different positions in said region of action, and said storage means are adapted for storing the complete system function data. This kind of acquisition is not much different, in particular with respect to the movement of the FFP through the region of action, i.e. with respect to the used trajectory, from the acquisition of signals from a (real) examination object, e.g. a patient, apart from the fact that according to the present invention the probe is moved (contrary to the examination object being stationary) to all positions of a grid covering the region of action.

According to further embodiments it is not mandatory to have the complete system function data already available (or to acquire it completely in order to generate processed system function data having a higher SNR), but it is also possible to start from an available subset of the complete system function data. To acquire only a subset of system function data the probe is not moved to all positions of a grid covering the region of action, but only a reduced set of points thereof.

According to one of these embodiments said processing means are adapted for combining, in particular averaging, signals acquired at different spatial positions, which share the same information due to the spatial symmetries, in particular spatial mirror symmetries, existing in the frequency components of an available subset of the complete system function data, and for reconstructing the complete system function from the combined signal by use of said spatial symmetries. For instance, half of the system function data could be acquired, and with this subset a step of averaging of the available system function data from two areas, e.g. two neighbouring quadrants or octants, could be performed. From these averaged system function data a complete system function data set could be determined by use of the additional information about the structure of the system function.

According to another embodiment said processing means are adapted for summing up frequency components of an available subset of the complete system function data with similar spatial information, and for reconstructing the complete system function from the summed up frequency components by use of said spatial information existing in the frequency components.

Many different options exist for the positions at which the probe is placed for the acquisition of the signals to acquire said subset of the system function data. According to advantageous embodiments the plurality of positions is located in a quadrant or an octant of said region of action or is distributed in an interleaved manner over the region of action.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE INVENTION

Figure 1:
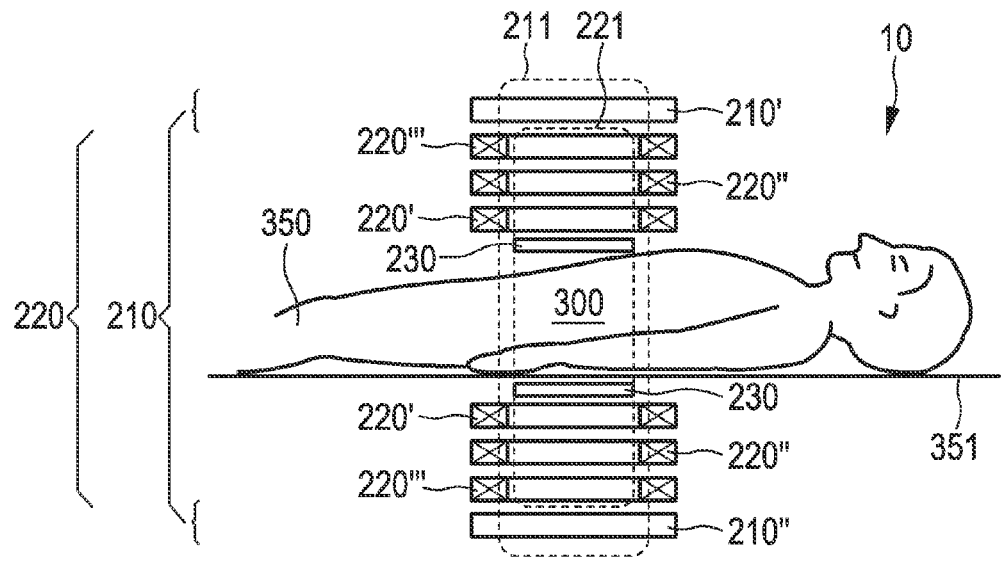
FIG. 1 shows an arrangement according to the present invention.

FIG. 1 shows an arbitrary object to be examined by means of an arrangement 10 according to the present invention is shown. The reference numeral 350 in FIG. 1 denotes an object, in this case a human or animal patient, who is arranged on a patient table, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

Figure 2:
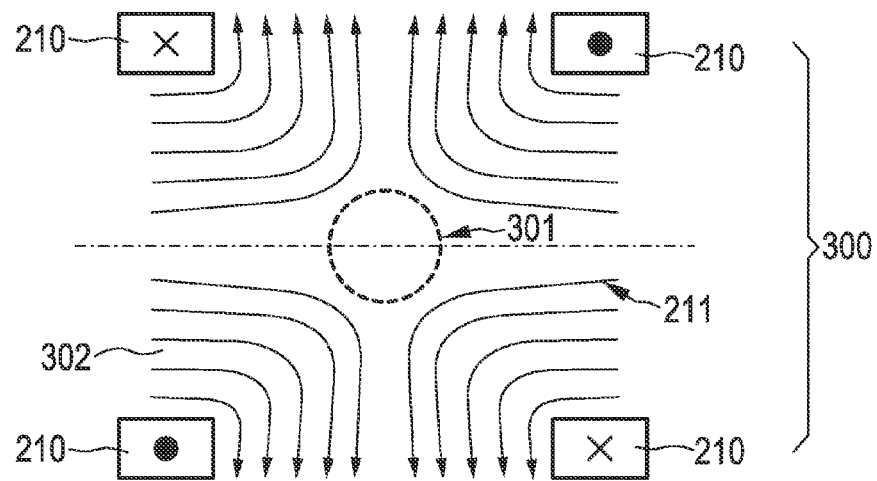
FIG. 2 shows an example of the field line pattern produced by an arrangement according to the present invention.

As an example of an embodiment of the present invention, an arrangement 10 is shown in FIG. 2 comprising a plurality of coils forming a selection means 210 whose range defines the region of action 300 which is also called the region of treatment 300. For example, the selection means 210 is arranged above and below the patient 350 or above and below the table top. For example, the selection means 210 comprise a first pair of coils 210', 210", each comprising two identically constructed windings 210' and 210" which are arranged coaxially above and below the patient 350 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of particles 100 present in that first sub-zone 301 is not saturated, whereas the magnetization of particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside the first sub-zone 301) the magnetic field strength is sufficiently strong to keep the particles 100 in a state of saturation. By changing the position of the two sub-zones 301, 302 within the region of action 300, the (overall) magnetization in the region of action 300 changes. By measuring the magnetization in the region of action 300 or a physical parameters influenced by the magnetization, information about the spatial distribution of the magnetic particles in the region of action can be obtained. In order to change the relative spatial position of the two sub-zones 301, 302 in the region of action 300, a further magnetic field, the so-called magnetic drive field 221, is superposed to the selection field 211 in the region of action 300 or at least in a part of the region of action 300.

Figure 3:
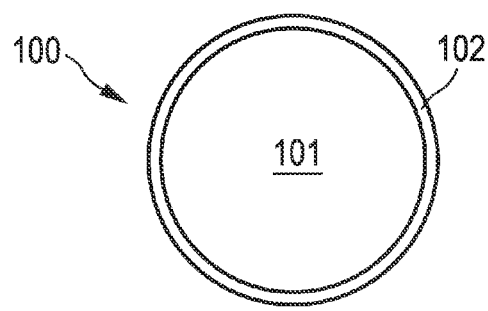
FIG. 3 shows an enlarged view of a magnetic particle present in the region of action.

FIG. 3 shows an example of a magnetic particle 100 of the kind used together with an arrangement 10 of the present invention. It comprises for example a spherical substrate 101, for example, of glass which is provided with a soft-magnetic layer 102 which has a thickness of, for example, 5 nm and consists, for example, of an iron-nickel alloy (for example, Permalloy). This layer may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 µm, a magnetic field of approximately 800 A/m (corresponding approximately to a flux density of 1 mT) is then required, whereas in the case of a diameter of 100 µm a magnetic field of 80 A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80 A/m and a gradient (in a given space direction) of the field strength of the magnetic selection field 211 amounting to $160 \cdot 10^3$ A/m2, the first sub-zone 301 in which the magnetization of the particles 100 is not saturated has dimensions of about 1 mm (in the given space direction).

When a further magnetic field—in the following called a magnetic drive field 221 is superposed on the magnetic selection field 210 (or gradient magnetic field 210) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics.

In order to generate these magnetic drive fields 221 for any given direction in space, there are provided three further coil pairs, namely a second coil pair 220', a third coil pair 220" and a fourth coil pair 220''' which together are called drive means 220 in the following. For example, the second coil pair 220' generates a component of the magnetic drive field 221 which extends in the direction of the coil axis of the first coil pair 210', 210" or the selection means 210, i.e. for example vertically. To this end the windings of the second coil pair 220' are traversed by equal currents in the same direction. The effect that can be achieved by means of the second coil pair 220' can in principle also be achieved by the superposition of currents in the same direction on the opposed, equal currents in the first coil pair 210', 210", so that the current decreases in one coil and increases in the other coil. However, and especially for the purpose of a signal interpretation with a higher signal to noise ratio, it may be advantageous when the temporally constant (or quasi constant) selection field 211 (also called gradient magnetic field) and the temporally variable vertical magnetic drive field are generated by separate coil pairs of the selection means 210 and of the drive means 220.

The two further coil pairs 220", 220''' are provided in order to generate components of the magnetic drive field 221 which extend in a different direction in space, e.g. horizontally in the longitudinal direction of the region of action 300 (or the patient 350) and in a direction perpendicular thereto. If third and fourth coil pairs 220", 220''' of the Helmholtz type (like the coil pairs for the selection means 210 and the drive means 220) were used for this purpose, these coil pairs would have to be arranged to the left and the right of the region of treatment or in front of and behind this region, respectively. This would affect the accessibility of the region of action 300 or the region of treatment 300. Therefore, the third and/or fourth magnetic coil pairs or coils 220", 220''' are also arranged above and below the region of action 300 and, therefore, their winding configuration must be different from that of the second coil pair 220'. Coils of this kind, however, are known from the field of magnetic resonance apparatus with open magnets (open MRI) in which a radio frequency (RF) coil pair is situated above and below the region of treatment, said RF coil pair being capable of generating a horizontal, temporally variable magnetic field. Therefore, the construction of such coils need not be further elaborated herein.

The arrangement 10 according to the present invention further comprise receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein.

In an alternative embodiment for the selection means 210 shown in FIG. 1, permanent magnets (not shown) can be used to generate the gradient magnetic selection field 211. In the space between two poles of such (opposing) permanent magnets (not shown) there is formed a magnetic field which is similar to that of FIG. 2, that is, when the opposing poles have the same polarity. In another alternative embodiment of the arrangement according to the present invention, the selection means 210 comprise both at least one permanent magnet and at least one coil 210', 210" as depicted in FIG. 2.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 25 kHz and approximately 100 kHz. The magnetic field variations that the receiving means are supposed to be sensitive are preferably in a frequency range of approximately 50 kHz to approximately 10 MHz.

Figure 4A:
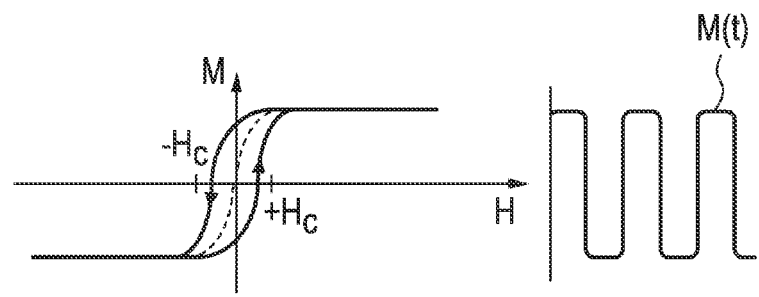
FIGS. 4a and 4b show the magnetization characteristics of such particles.
Figure 4B:
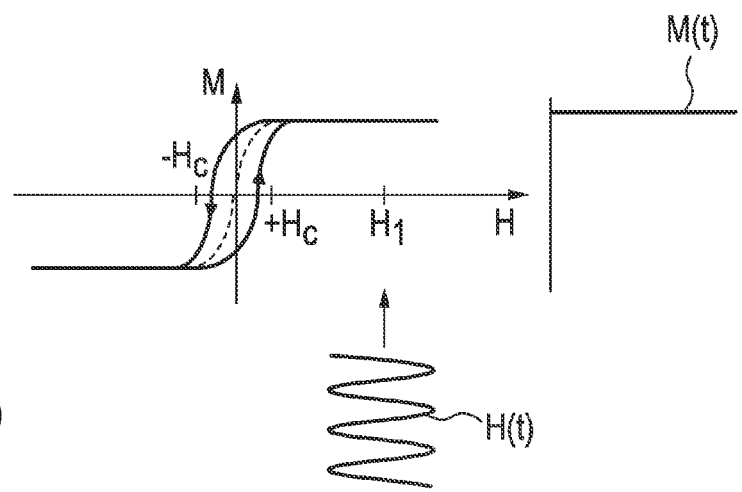

FIGS. 4a and 4b show the magnetization characteristic, that is, the variation of the magnetization M of a particle 100 (not shown in FIGS. 4a and 4b) as a function of the field strength H at the location of that particle 100, in a dispersion with such particles. It appears that the magnetization M no longer changes beyond a field strength $+H_c$ and below a field strength $-H_c$, which means that a saturated magnetization is reached. The magnetization M is not saturated between the values $+H_c$ and $-H_c$.

FIG. 4a illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particles 100 for this condition reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

Figure 5:
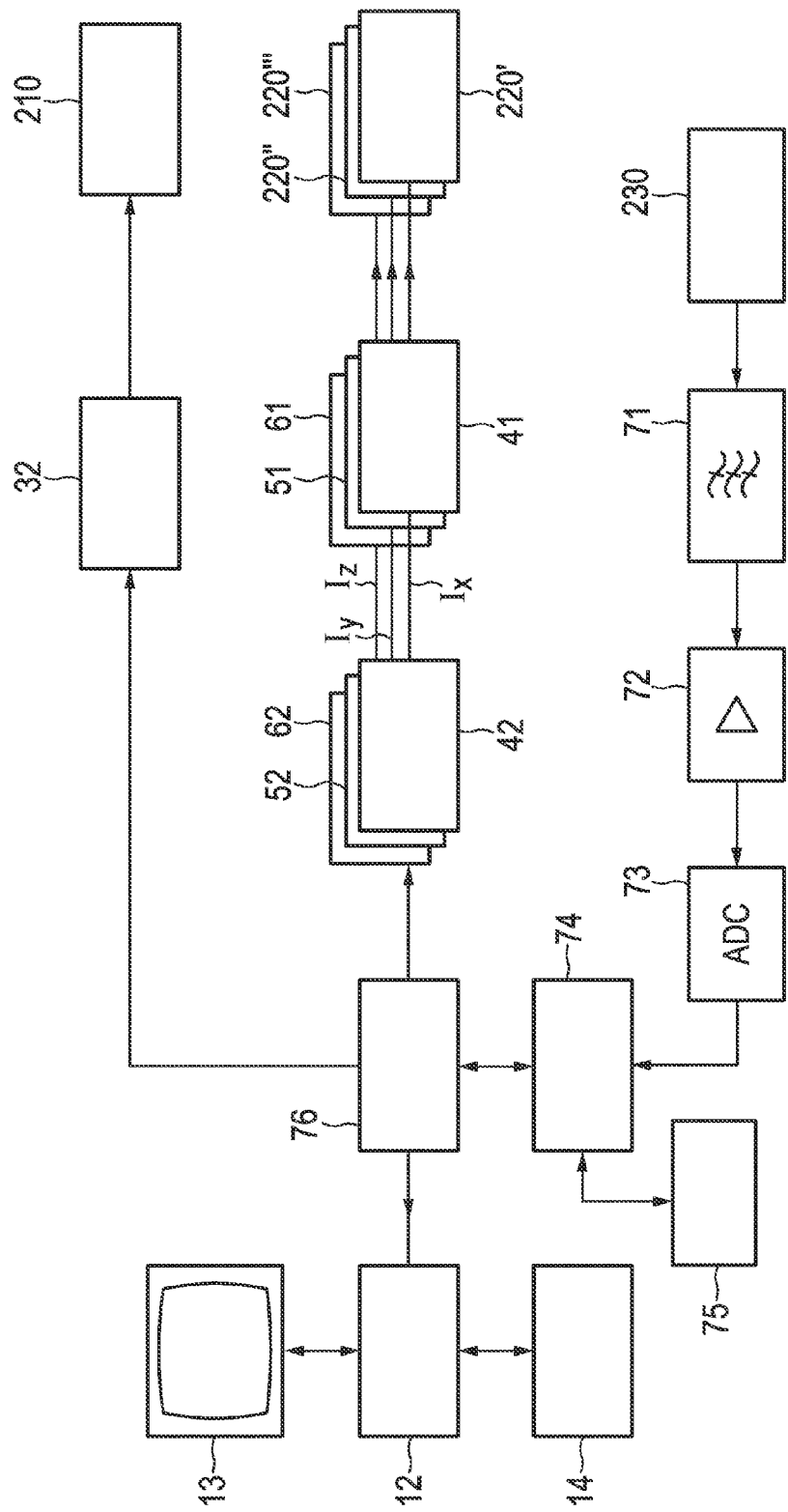
FIG. 5 shows a block diagram of the apparatus according to the present invention.

FIG. 5 shows a block diagram of the apparatus 10 shown in FIG. 1. The coil pair 210', 210" is shown schematically in FIG. 5 and bears the reference 210 for the sake of clarity. The coil pair (first magnetic means) 210 is supplied with a DC current from a controllable current source 32, said current source being controlled by a control unit 76. The control unit 76 is connected to a computer 12 which is coupled to a monitor 13 for displaying the distribution of magnetic particles in the examination area and an input unit 14, for example a keyboard 14.

The coil pairs (second magnetic means) 220', 220", 220''' are connected to current amplifiers 41, 51, 61, from which they receive their currents. The current amplifiers 41, 51, 61 are in turn in each case connected to an AC current source 42, 52, 62 which defines the temporal course of the currents Ix, Iy, Iz to be amplified. The AC current sources 42, 52, 62 are controlled by the control unit 76.

The receiving coil (receiving means) 230 is also shown schematically in FIG. 5. The signals induced in the receiving coil 230 are fed to a filter unit 71, by means of which the signals are filtered. The aim of this filtering is to separate measured values, which are caused by the magnetization in the examination area which is influenced by the change in position of the two part-regions (301, 302), from other, interfering signals. To this end, the filter unit 71 may be designed for example such that signals which have temporal frequencies that are smaller than the temporal frequencies with which the coil pairs 220', 220", 220''' are operated, or smaller than twice these temporal frequencies, do not pass the filter unit 71. The signals are then transmitted via an amplifier unit 72 to an analog/digital converter 73 (ADC). The digitalized signals produced by the analog/digital converter 73 are fed to an image processing unit (also called reconstruction means) 74, which reconstructs the spatial distribution of the magnetic particles from these signals and the respective position which the first part-region 301 of the first magnetic field in the examination area assumed during receipt of the respective signal and which the image processing unit 74 obtains from the control unit 76. The reconstructed spatial distribution of the magnetic particles is finally transmitted via the control unit 76 to the computer 12, which displays it on the monitor 13.

The apparatus comprises also storage means 75, e.g. a hard disk or a semiconductor memory, coupled to the image processing unit 74 for storing the acquired detection signals and system function data of the apparatus 10.

According to the present invention the storage means 75 are adapted for storing at least a subset of measured system function data of the arrangement's system function, said system function comprising a system function data set describing the relation between spatial position of the magnetic material and the system response for said arrangement and the trajectory along which said first sub-zone (FFP) is moved for the acquisition of said system function data. The processing means 74 (which can be implemented as hardware, software or a mix thereof) are adapted for generating processed system function data having a higher SNR than said measured system function data by processing said measured system function data using additional knowledge about the structure of the system function. Reconstruction means, which are in this embodiment implemented by the same unit 74 as the processing means but could also be implemented as separate unit, are adapted for reconstructing the spatial distribution of the magnetic material in the region of action from the detection signals and said processed system function data.

As explained above MPI applies a new method of signal encoding based on the dynamic displacement of a localized excitation process and allows fast volumetric imaging. However, in contrast to established imaging modalities like MRI and CT, no simple mathematical transform has yet been identified to reconstruct images from the acquired data. Therefore, MPI image reconstruction requires knowledge of a "system function" describing the system response to a given spatial distribution of particles, i.e., mapping particle position to frequency response. To solve the reconstruction problem, the system function has to be inverted, usually requiring some regularization scheme.

To date, the system function is determined experimentally by measuring the magnetization response of a point-like sample at a large number of spatial positions corresponding to the number of image pixels or voxels. This calibration procedure requires very long acquisition times and furthermore provides a system function that is contaminated with noise. Due to the large size of the system function matrix, solving the inverse reconstruction problem is also quite time-consuming and claims large amounts of computer memory.

From a theoretical understanding of the signal encoding process one expects to gain insight into the structure of the system function. This knowledge can be used to speed up the system function acquisition or to even simulate parts or all of the system function. Information about the matrix structure can furthermore help to find more compact system function representations, helping to reduce memory requirements and speed up reconstruction. Finally, identification of a mathematical transform leading from the data to the image would greatly simply the reconstruction process.

Next, signal generation shall be described. The basic principle of signal generation in MPI relies on the non-linear magnetization response M(H) of ferromagnetic particles to an applied magnetic field H. An oscillating drive field $H_D(t)$ of sufficient amplitude leads to a magnetization response M(t) of the particles, which has a different spectrum of higher harmonics than the drive field. If, for instance, a harmonic drive field is used, the drive field spectrum only contains the base frequency, whereas the particle response also contains multiples of the base frequency. The information contained in these higher harmonics is used for MPI. Experimentally, the time-dependent change in particle magnetization is measured via the induced voltage in receive coils. Assuming a single receive coil with sensitivity $S_r(r)$, the changing magnetization induces a voltage $$V(t) = -\mu_0 \frac{d}{dt} \int_{object} S_r(r) \cdot M(r, t) d^3 r \tag{1}$$

according to Faraday's law. $\mu_0$ is the magnetic permeability of vacuum. The receive coil sensitivity $S_r(r) = H_r(r)/I_0$ derives from the field $H_r(r)$ the coil would produce if driven with a unit current $I_0$. In the following, the sensitivity of the receive coil is approximated to be homogeneous over the region of interest, i.e., $S_r(r)$ is constant. If $M_x(r,t)$ is the magnetization component picked up by a receive coil in x direction, the detected signal can be written as $$V(t) \propto -\frac{d}{dt} \int_{object} M_x(r, t) d^3 r. \tag{2}$$

Figure 6A:
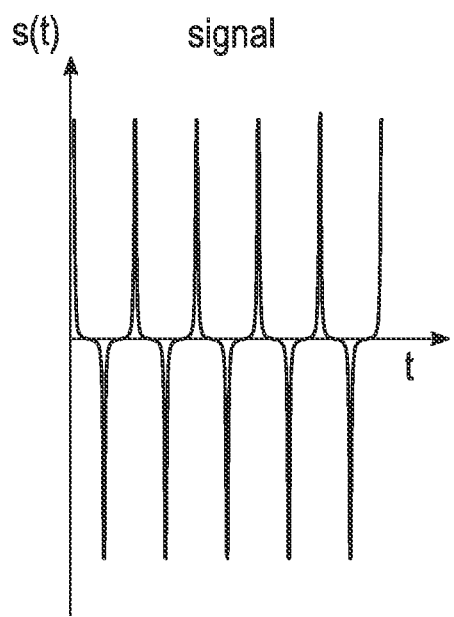
FIG. 6 shows a time-dependent detection signal s(t) and its spectrum $S_n$.

Now, consider the signal s(r,t) generated by a point-like distribution of particles. The volume integration can be removed and the particle magnetization $M_x(r,t)$ is determined by the local field H(r,t). For the moment, the field is assumed to have only one spatial component $H_x(r,t)$, which is pointing in receive-coil direction. The signal (shown in FIG. 6a) can then be written as $$s(r, t) = -\frac{d}{dt} M(r, t) = -\frac{d}{dt} M(H(r, t)) \tag{3}$$
$$= -\frac{\partial M}{\partial H} \frac{dH(r, t)}{dt} = -M'(H) \frac{dH(r, t)}{dt},$$

Figure 6B:
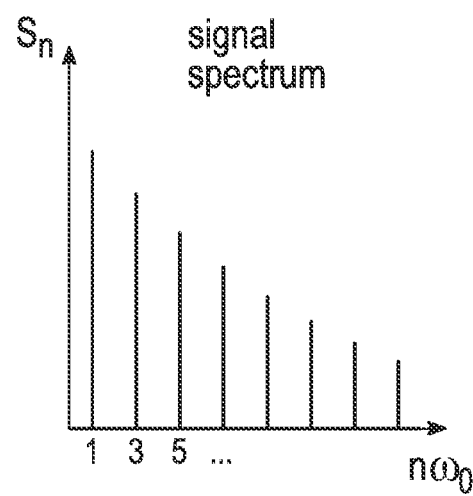

Since this equation holds for all orientations where the field is aligned with the direction of the acquired magnetization component, the subscript x has been omitted. Equation 3 shows that high signal results from the combination of a steep magnetization curve with rapid field variations. Fourier expansion of the periodic signal s(t) generated by applying a homogeneous drive field $H(r,t)=H_D(t)$ yields the signal spectrum $S_n$, as shown in FIG. 6b. Intensity and weight of higher harmonics in the spectrum are related to the shape of the magnetization curve M(H), and to the waveform and amplitude of the drive field $H_D(t)$. To illustrate their influence on the spectrum, a number of representative cases are shown in FIG. 7.

The step function relates to an immediate particle response and creates a spectrum that is rich in high harmonics. The spectral components have constant magnitude at odd multiples of the drive frequency. Even harmonics are missing due to the sine-type pattern of the time signal s(t). The step function corresponds to an ideal particle response and represents the limiting case for the achievable weight of higher harmonics. For this magnetization curve, triangle and sine drive fields yield the same result.

If the particle response to the drive field is slowed down by introducing a linear range in the magnetization curve, the relative weight of higher harmonics is reduced. Thereby, the harmonic drive field performs better than the triangular excitation, since it sweeps faster over the linear range.

Figure 7:
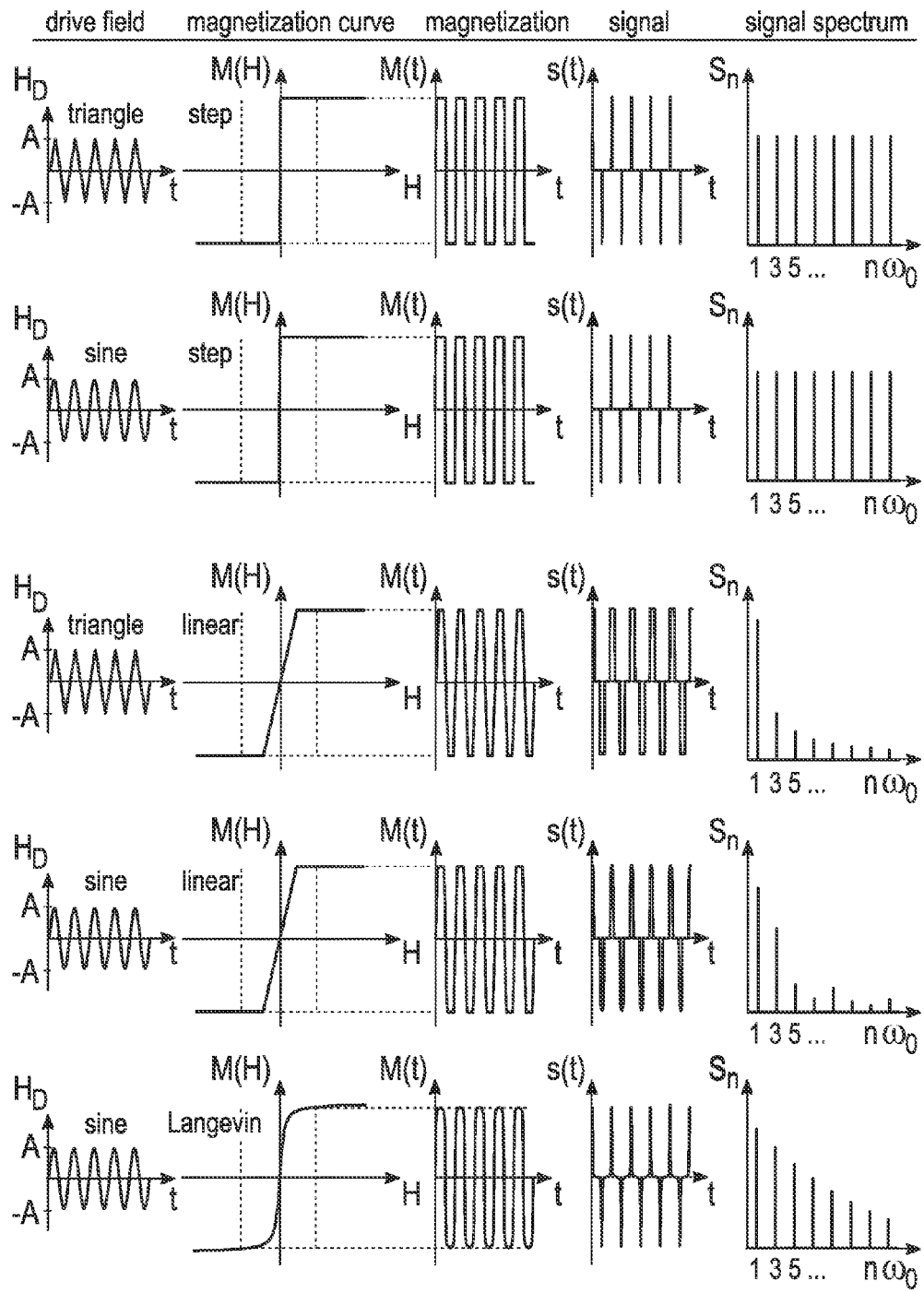
FIG. 7 shows the particle magnetization response M(t), acquired time signal s(t), and magnitude spectral components $S_n$ for different drive fields and particle magnetization curves.

The last row in FIG. 7 shows a more realistic particle magnetization as given by the Langevin function $$M(\xi)=M_0(coth\xi-1/\xi), \quad (4)$$

where $\xi$ is the ratio between magnetic energy of a particle with magnetic moment m in an external field H, and thermal energy:

$$\xi = \frac{mH}{kT}. \quad (5)$$

A higher magnetic moment results in a steeper magnetization curve and creates more higher harmonics for a given drive field amplitude. Alternatively, high harmonics can be generated from a shallow curve using faster field variations, e.g., induced by a higher drive field amplitude. It should be noted that MPI uses ferromagnetic particles to obtain a sufficiently steep magnetization curve. For low concentrations, however, their mutual interactions can be neglected and they can be treated like a gas of paramagnetic particles with extremely large magnetic moment, a phenomenon also known as "super-paramagnetism".

Next, 1D spatial encoding shall be described. To encode spatial information in the signal, a static magnetic gradient field $H_s(r)$, also called selection field, is introduced. For 1D encoding, the selection field has a non-zero gradient only in x direction, $G_x=dH_s/dx$. If the gradient is non-zero over the complete FOV, the selection field can only be zero in a single point, the "field-free point". In regions far away from the FFP, the particle magnetization is driven into saturation by the selection field.

Application of a spatially homogeneous and temporally periodic drive field $H_D(t)$ in addition to the selection field $H_s(r)$ corresponds to a periodic displacement of the FFP along the gradient direction. The particles experience a local field $$H(x,t)=H_S(x)-H_D(t), \quad (6)$$

The minus sign has been chosen to make later calculations more convenient. Since the FFP sweeps over each spatial position x at a different point in time, each position can be identified by its characteristic spectral response.

Figure 8:
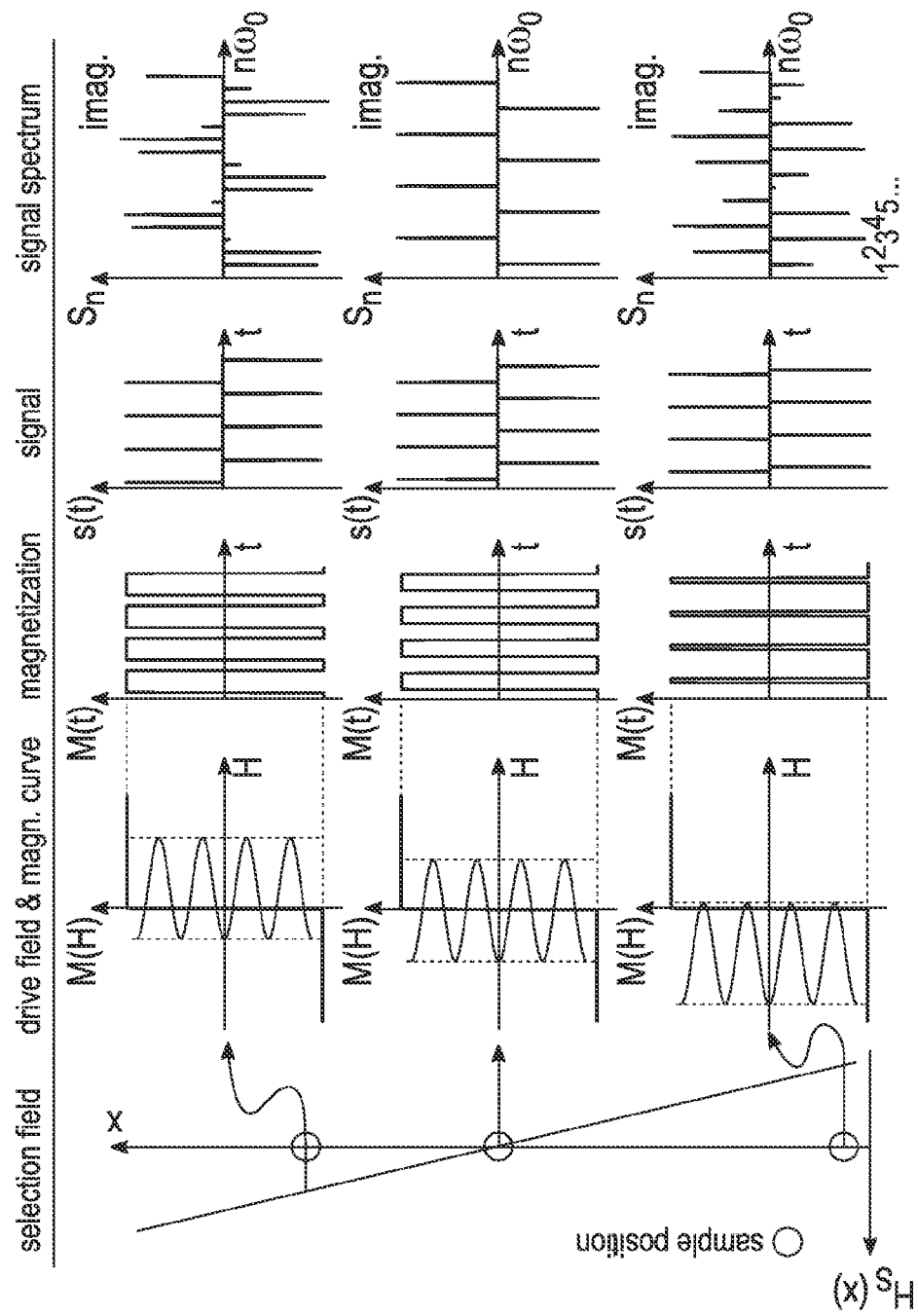
FIG. 8 shows diagrams illustrating the relation between ideal particle response and selection field offset.
Figure 9:
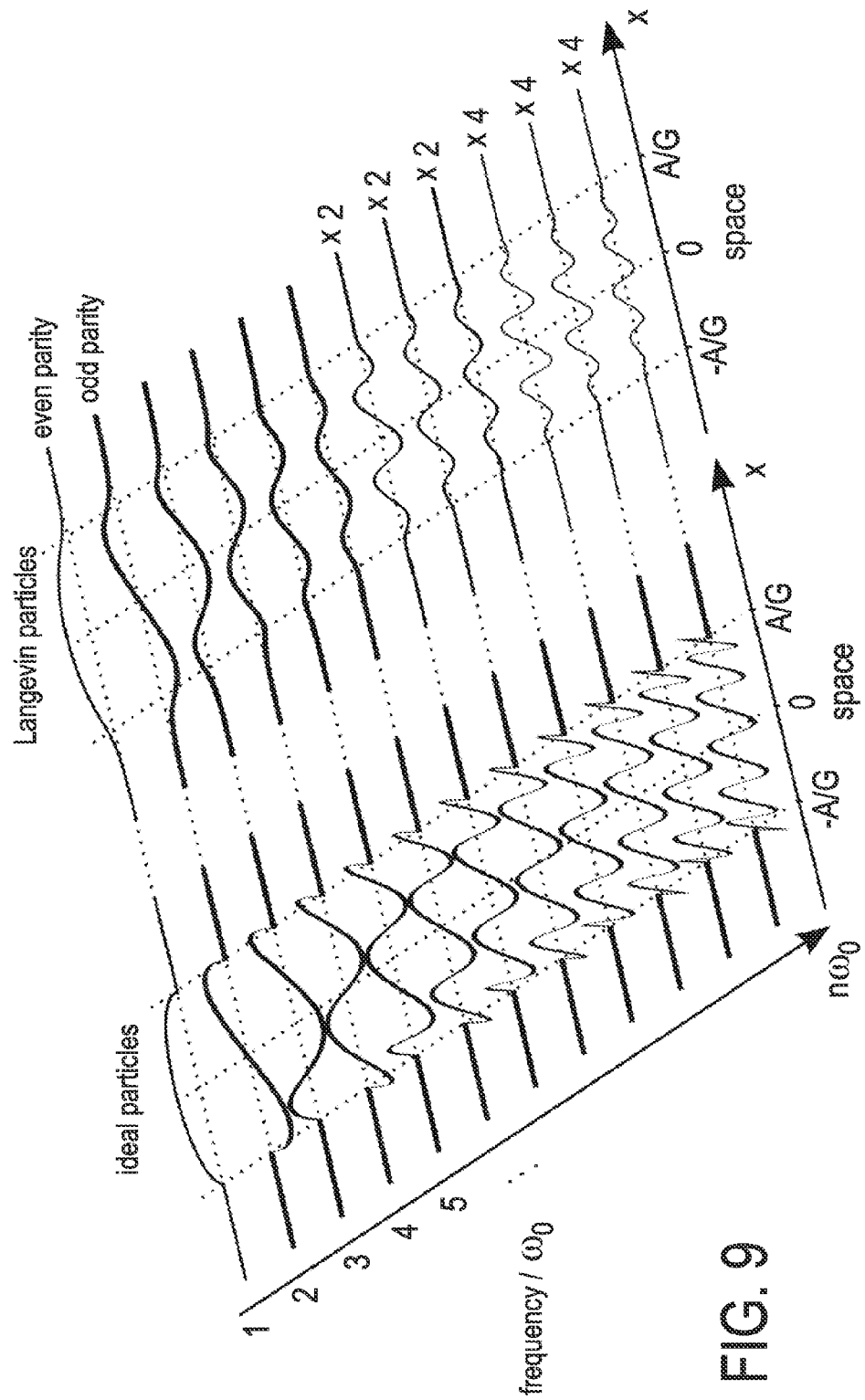
FIG. 9 shows diagrams illustrating the spatial dependence of spectral signal components for a harmonic drive field in combination with a constant gradient selection field.

In the following details of the harmonic drive field and ideal particles shall be described. FIG. 8 shows spectra at three different spatial positions generated by ideal particles exposed to a selection field $H_s$ of constant gradient strength G and a harmonic drive field $H_D$ of frequency $\omega_0$ and amplitude A. For the nth harmonic, corresponding to the nth component of a Fourier series expansion, one finds the following dependence on particle position x:

$$S_n^{ideal}(x) = -\frac{4M_0}{T}i\sin\left(n\arccos\frac{Gx}{A}\right) \quad (7)$$

$$= -\frac{4M_0}{T}iU_{n-1}(Gx/A)\sqrt{1-(Gx/A)^2},$$

$$n = 1, 2, 3, \ldots ,$$

where the $U_n(x)$ represent Chebyshev polynomials of the second kind. The functions are defined in the range $-A/G<x<A/G$. A cosine drive field has been used instead of the sine drive field to arrive at a simpler expression. The spatial dependence for the first harmonics is plotted in the left part of FIG. 9. One finds an increasing number of oscillations with increasing frequency components n. This relates to the fact that Chebyshev polynomials form a complete orthogonal basis set, so that any particle distribution C(x) can be expanded into these functions. Successive frequency components have alternating spatial parity with respect to the center of the FOV (even/odd).

The $S_n(x)$ can be seen as a sensitivity map, describing the spatial sensitivity profile of each frequency component n. In an MPI experiment, a particle distribution C(x) generates spectral signal components $$V_n = \int_{FOV} S_n(x)C(x)dx, n = 1, 2, 3, \ldots . \quad (8)$$

Thus, the $S_n(x)$ represent the system function. The system function not only describes the spatial signal dependence, but also contains information about the particles' magnetization curve and system parameters (e.g. drive field amplitude A and frequency $\omega_0=2\pi/T$, selection field gradient G).

Using equation (7), the spectral signal components (equation (8)) for ideal particles can be written as $$V_n = -\frac{4M_0}{T}i\int_{-A/G}^{A/G} C(x)U_{n-1}(Gx/A)\sqrt{1-(Gx/A)^2}\,dx. \quad (9)$$

In this notation, the $V_n$ correspond to coefficients of a Chebyshev series. It follows that the particle concentration can be reconstructed by doing a Chebyshev transform of the measured $V_n$, i.e., by evaluating the Chebyshev series $$C(x) = \frac{2}{\pi}\frac{G}{A}\frac{Ti}{4M_0}\sum_{n=1}^{\infty} U_{n-1}(Gx/A)V_n. \quad (10)$$

Hence, for ideal particles under the influence of a harmonic drive field and a constant selection field gradient, reconstruction of the spatial particle distribution simply corresponds to calculating the sum over the measured harmonics $V_n$ weighted with Chebyshev polynomials of the second kind. In terms of the system function $S_n^{ieal}$ (x), the particle concentration can be written as $$C(x) = -\frac{2}{\pi}\frac{G}{A}\left(\frac{T}{4M_0}\right)^2 \frac{1}{\sqrt{1-(Gx/A)^2}}\sum_{n=1}^{\infty} S_n^{ideal}(x)V_n. \qquad (11)$$

Next, details of the harmonic drive field and Langevin particles will be described. For more realistic particles, the system function is given by a spatial convolution between the derivative of the magnetization curve, M'(H$_s$), and the Chebyshev components:

$$S_n(x) = \frac{1}{2M_0}M'(Gx)*S_n^{ideal}(x). \qquad (12)$$

Depending on the steepness of M(H), the $S_n(x)$ will be a blurred version of the $S_n^{ideal}$ (x), extending slightly beyond the interval which is covered by the FFP motion and to which the $S_n^{ideal}$ (x) are confined. Thus, particles that are located slightly outside the range accessed by the FFP also generate signal. The right part of FIG. 9 displays components of the system function for particles following the Langevin magnetization curve in a constant selection field gradient.

In the measurement process according to equation (8), the FOV now refers to the range where the $S_n(x)$ are non-zero. A sufficiently steep magnetization curve can provide confinement to a region not much larger than range covered by the FFP, i.e., −A/G<x<A/G.

Since the system function components cannot be sharper than the convolution kernel, an MPI experiment with Langevin particles will run into a resolution limit correlating with the width of M'(x). However, if the magnetization curve is known, deconvolution of the kernel M'(x) from the image can be used to regain full resolution. Since the derivative of the magnetization curve is a symmetric function M'(x)=M'(−x), one can use equation (12) to show that $$V_n = \int_{FOV} S_n(x)C(x)dx$$

$$= \frac{1}{2M_0}\int_{FOV}[M'(Gx)*S_n^{ideal}(x)]C(x)dx$$

$$= \frac{1}{2M_0}\int_{FOV}\left[\int_{-A/G}^{A/G}M'(G(x-\tilde{x}))S_n^{ideal}(\tilde{x})d\tilde{x}\right]C(x)dx$$

$$= \frac{1}{2M_0}\int_{-A/G}^{A/G}S_n^{ideal}(\tilde{x})\left[\int_{FOV}M'(G(\tilde{x}-x))C(x)dx\right]d\tilde{x} \qquad (13)$$

$$= \int_{-A/G}^{A/G}S_n^{ideal}\tilde{C}(x)dx, \qquad (14)$$

where $\tilde{C}(x)$ corresponds to the expression in square brackets in equation (13). Since equation (14) corresponds to equation (9), reconstruction for the harmonic drive field is given by equation (11), i.e., $$\tilde{C}(x) = -\frac{2}{\pi}\frac{G}{A}\left(\frac{T}{4M_0}\right)^2\frac{1}{\sqrt{1-(Gx/A)^2}}\sum_{n=1}^{\infty}S_n^{ideal}(x)V_n. \qquad (15)$$

This means, that in the interval where the ideal particle system function $S_n^{ideal}$ (x) is defined, i.e., −A/G<x<A/G, $\tilde{C}$(x) can be directly reconstructed. If the particle concentration C(x) is confined to the FOV, $\tilde{C}$(x) is just the convolution of C(x) with M'(x):

$$\tilde{C}(x) = \frac{1}{2M_0}[M'(x)*C(x)]. \qquad (16)$$

Thus, the exact concentration distribution C(x) can then be derived by deconvolving the kernel M'(x) from $\tilde{C}$(x). However, as discussed above, reconstruction using equation (15) only yields $\tilde{C}$(x) on the interval −A/G<x<A/G which is covered by the FFP motion. If the particle concentration exceeds this range, deconvolution requires additional knowledge about the concentration beyond the edges the FFP range.

On the other hand, deconvolution is not mandatory. Provided that the particle magnetization curve M(H) is sufficiently steep, the modified concentration distribution $\tilde{C}$(x) may already satisfy resolution requirements of many applications.

Next, details of a triangular drive field will be explained. An illustrative case is to use a triangular drive field instead of the harmonic field. The system function for ideal particles then has the form $$S_n^{ideal}(x) = -\frac{4M_0}{T}i\sin\left(n\frac{\pi}{2}\frac{G}{A}x\right). \qquad (17)$$

for an FFP motion covering the range 0<x<2A/G. Now, instead of the Chebyshev series, a Fourier series can be used to reconstruct a particle concentration:

$$C(x) = \frac{G}{A}\frac{Ti}{4M_0}\sum_{n=1}^{\infty}\sin\left(n\frac{\pi}{2}\frac{G}{A}x\right)V_n. \qquad (18)$$

The measured frequency components $V_n$ are proportional to components $\tilde{C}$(k) in k space, which are related to the spatial distribution C(x) by Fourier transformation. In terms of the system function, equation (18) becomes $$C(x) = -\frac{G}{A}\left(\frac{T}{4M_0}\right)^2\sum_{n=1}^{\infty}S_n^{ideal}(x)V_n. \qquad (19)$$

For realistic particles, the system function has to be convolved with M'(H$_s$). Since equations (12-14) derived for harmonic drive field excitation hold for the triangular system function as well, a modified/convolved concentration $\tilde{C}$(x) can be reconstructed in the range 0<x<2A/G.

Next, a matrix formulation will be explained. For MPI image reconstruction, the continuous spatial distribution of particles will be mapped to a grid, where each grid location represents a small spatial region. Furthermore, only a limited number n of frequency components is recorded. If the spatial positions are indexed with m, distcomp becomes $$V_n = \sum_m S_{nm}C_m, \qquad (20)$$

or, in vector/matrix formulation, $$v = Sc. \qquad (21)$$

Calculation of the concentration vector then basically corresponds to an inversion of matrix S:

$$c = S^{-1}v. \quad (22)$$

This notation will be used for 2D or 3D imaging as well, which requires collapsing spatial indices into the single index m. Thus, concentration is always a vector, independent of spatial dimension.

Going back to the 1D case for a harmonic drive field, introduction of a scalar $$\alpha = -\frac{2}{\pi}\frac{G}{A}\left(\frac{T}{4M_0}\right)^2 \quad (23)$$

and a diagonal matrix $$\beta_{mn} = \frac{1}{\sqrt{1-(Gx_m/A)^2}}, \beta_{mn} = 0 \text{ for } n \neq m, \quad (24)$$

allows derivation of the following identity by comparing equation (22) with equation (11):

$$S^{-1} = \alpha\beta S^T. \quad (25)$$

Thus, in the case of 1D imaging of ideal particles, the inverse matrix can simply be obtained by multiplication of the transpose with a scalar and a diagonal matrix.

Using only a limited number of frequency components corresponds to working with a truncated Chebyshev series. The Chebyshev truncation theorem then states that the error in approximating the real concentration distribution is bounded by the sum of the absolute values of the neglected coefficients. More importantly, for reasonably smooth distributions, the error is on the order of the last retained Chebyshev coefficient.

Next, 2D and 3D spatial encoding will be described.

First, a 1D drive field is described. A first step towards describing 2D and 3D imaging is to look at the 3D system function of particles in a 3D selection field $H_s(r)$ combined with a 1D drive field $H_D(t)$. Using a harmonic drive field and choosing a Maxwell coil setup to create a selection field as, the total field can be approximated by $$H(r,t) = H_S(r) - H_D(t) = \begin{pmatrix} Gx \\ Gy \\ 2Gz \end{pmatrix} - \begin{pmatrix} 0 \\ 0 \\ A\cos\omega t \end{pmatrix}. \quad (26)$$

The system function can be written as a convolution over the z component of the selection field $$S_n = -\frac{2i}{T}\frac{\partial M(H_S)}{\partial H_z} * \left[U_{n-1}(H_{Sz}/A)\sqrt{1-(H_{Sz}/A)^2}\right]. \quad (27)$$

In this vector, each component refers to the signal induced by the respective x/y/z magnetization component. Detection of these components requires three orthogonal (sets of) receive coils.

For ideal particles, the explicit spatial dependence becomes $$S_n(r) = -\frac{2i}{T}\frac{M_0}{G}\left[\frac{1}{(x^2+y^2+4z^2)^{3/2}}\begin{pmatrix} -xz \\ -yz \\ x^2+y^2 \end{pmatrix}\right] * \left[U_{n-1}(2Gz/A)\sqrt{1-(2Gz/A)^2}\right]. \quad (28)$$

where the asterisk denotes convolution over the z component, i.e., the direction of the FFP motion resulting from the drive field. Thus, an expression describing the 3D spatial dependence of the respective magnetization component is convolved in drive field direction with the set of 1D Chebyshev functions.

Figure 10:
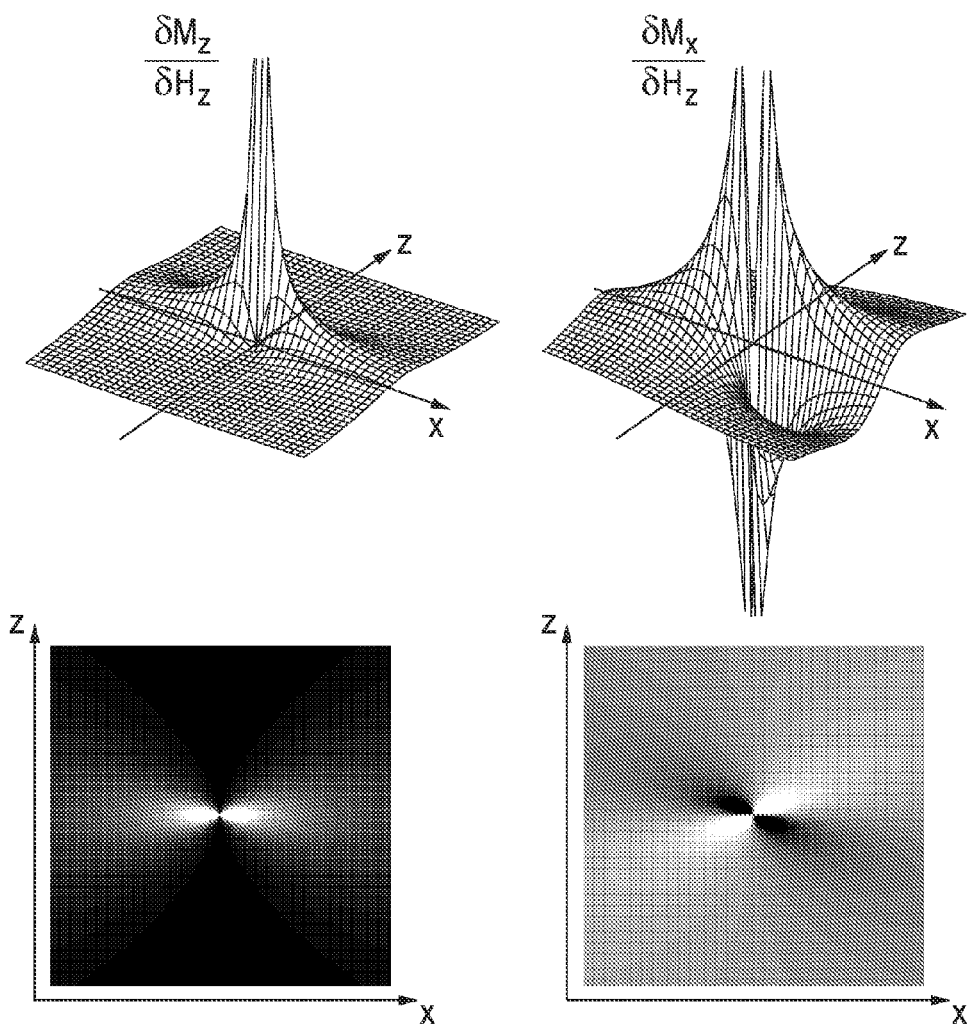
FIG. 10 shows diagrams illustrating the derivative of ideal particle magnetization with respect to the $H_z$ field component.

The shape of the convolution kernel is determined by a $\partial M/\partial H_z$, which describes how the magnetization responds to the drive field change. For ideal particles, it is singular at the origin. FIG. 10 shows the xz plane of the 3D kernel for the signal components detected in x and z direction, $S_{n,x}(r)$ and $S_{n,z}(r)$, respectively. Along the center line in drive field direction, the kernel for the $M_z$ magnetization corresponds to the delta distribution, just as in the 1D situation. With increasing distance from the center line, the kernel broadens and its amplitude decreases rapidly. For $M_x$, and for symmetry reasons also for $M_y$, the kernel is zero on the symmetry axes. It has high amplitude close to the singularity at the origin.

To form the 3D ideal particle system function, the 3D kernel is convolved along the drive field direction with the 1D Chebyshev polynomials 1ddrive3dsysfunc.

Figure 11:
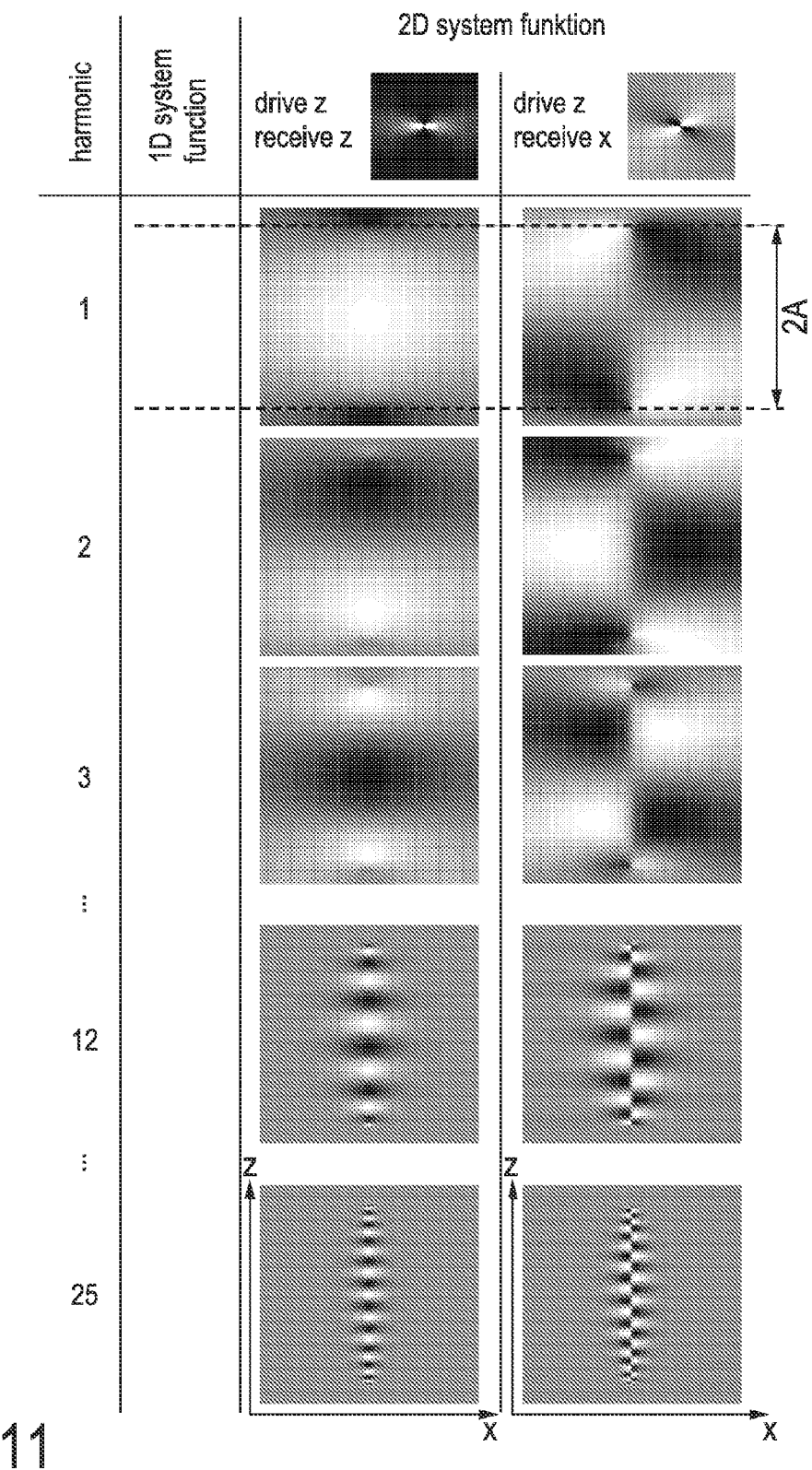
FIG. 11 shows diagrams illustrating the ideal particle system function at different harmonics for 1D FFP motion along the center line in z direction.

FIG. 11 shows central 2D slices extracted from selected harmonics for the above case of 1D drive field motion in z direction. Directly on the line covered by the FFP trajectory, the system function is given by Chebyshev polynomials and therefore can encode an arbitrary particle distribution, as discussed for the 1D situation. With increasing distance to the center line, the convolution kernel has an increasing blurring effect, so that finer structures of the higher Chebyshev polynomials are averaged to zero. Therefore, the signal in higher system function components condenses to the line of the FFP trajectory (cf. FIG. 11, harmonic 12 and 25), where the blurring effect is low. This can be explained by the fact that only in the close vicinity of the FFP, the field change is rapid enough to stimulate a particle response that generates high frequency components.

In an MPI experiment, it can be useful to exploit symmetries in the system function to partially synthesize the system function and thus speed up its acquisition and reduce memory requirements. From the 3D response to the 1D FFP motion, two basic rules can be derived for the parity of the system function in the spatial direction indexed with $i \in \{x,y,z\}$.

1. The "base" parity is given by the parity of the convolution kernel shown in FIG. 10. It is even, if the receive direction $j \in \{x,y,z\}$ is aligned with the drive direction $k \in \{x,y,z\}$. This corresponds to the magnetization derivative component $\partial M_j/\partial H_k$ for $j=k$. Otherwise kernel parity is odd:

$$p_{kernel} = \begin{cases} 1, & j=k \\ -1, & j \neq k. \end{cases} \quad (29)$$

2. If the spatial direction of interest is a drive field direction, i.e., i=k, then parity alternates between successive harmonics h of that drive field component:

$$p_{Cheb} = \begin{cases} (-1)^{(h+1)}, & i = k \\ 1, & i \neq k. \end{cases} \quad (30)$$

The reason is the alternating parity of the Chebyshev polynomials in the 1D system function.

Parity observed for harmonic h in a spatial direction i then is $p_{i,j,k,h} = p_{Cheb} \cdot p_{kernel}$.

Now, a 2D and 3D drive field will be described. From FIG. 11 it is clear that spatial encoding over the full extension of the FOV cannot be achieved using a 1D FFP motion. Thus for 2D or 3D spatial encoding, a drive field has to be added for each spatial direction to be encoded. For a simple implementation, one can choose harmonic drive fields with slight frequency differences in the different spatial directions, causing the FFP motion to follow a 2D or 3D Lissajous pattern. FIG. 11 furthermore showed that high resolution is only obtained in the close vicinity of the FFP trajectory line. Thus, the Lissajous pattern should be sufficiently dense to achieve homogeneous resolution.

Figure 12:
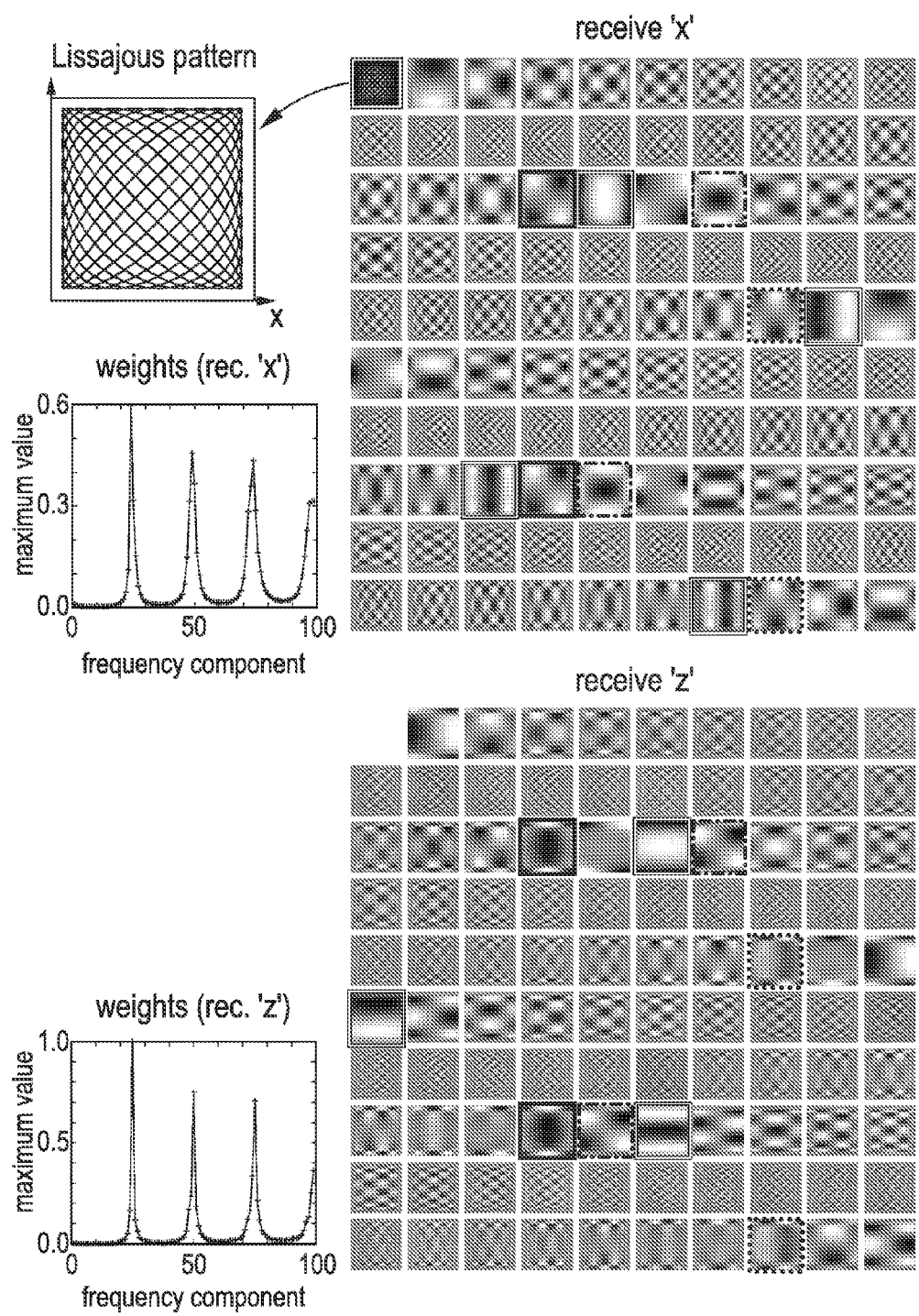
FIG. 12 shows diagrams illustrating successive frequency components of the ideal particle system function for 2D Lissajous FFP motion with an x/z frequency ratio of 24/25.

FIG. 12 displays a 2D Lissajous pattern generated by the superposition of two orthogonal harmonic drive fields with frequency ratio $\omega_x/\omega_z = 24/25$:

$$H_D(t) = \begin{pmatrix} A_x \cos\omega_x t \\ 0 \\ A_z \cos\omega_z t \end{pmatrix}. \quad (31)$$

Using a 3D selection field according to 1Ddrive, the doubled selection field gradient in z direction requires $A_z = 2A_x$ to cover a quadratic FOV with the FFP motion. FIG. 12 displays the first components of a simulated 2D system function for ideal particles exposed to the superposition of the 2D Lissajous drive field and the 3D selection field. Each receive direction has its own set of system functions, denoted by 'receive x' and 'receive z'. Components corresponding to higher harmonics of the respective drive frequency are indicated by double line frames. On the x channel, they have a spacing of 24 components. In the spatial x direction, they closely resemble the 1D Chebyshev series, while in z direction, they show no spatial variation. On the z channel, harmonics of the drive frequency exhibit a spacing of 25 components with a spatial pattern that is basically rotated by 90 degrees with respect to the x components.

While components corresponding to harmonics of the drive field frequencies only allow 1D encoding in the respective drive field direction, components arising from a mixture of both drive frequencies provide spatial variation in both directions at the same time. For instance, moving to the left from the first x drive-field harmonic on the x channel (component 24) corresponds to mix frequencies $m\omega_x + n(\omega_x - \omega_z)$ with increasing integer n and m=1. For larger m, one starts at a higher harmonic m. Moving to the right corresponds to negative n. Thus, pure drive field harmonics and their vicinity relate to low mixing orders, while increasing distance goes along with larger n and higher mixing orders.

It should be noted that the system function component observed for $m\omega_x + n(\omega_x - \omega_z)$ appears a second time at frequency $m\omega_x + n(\omega_x + \omega_z)$. Thus every component corresponding to frequency mixes appears twice. Examples are components 23 and 73 (m=1, n=1, bold frames) or 47 and 97 (m=2, n=1, dotted frames), but also 26 and 74 (m=1, n=−2, dashed frames) on the x channel.

FIG. 12 also plots the maximum intensities (weights) of the generated system function components. Highest intensities are found in the higher harmonics of the drive frequencies, however with a decrease towards higher frequencies. Components corresponding to mix frequencies have much lower intensity than pure harmonics.

Figure 13:
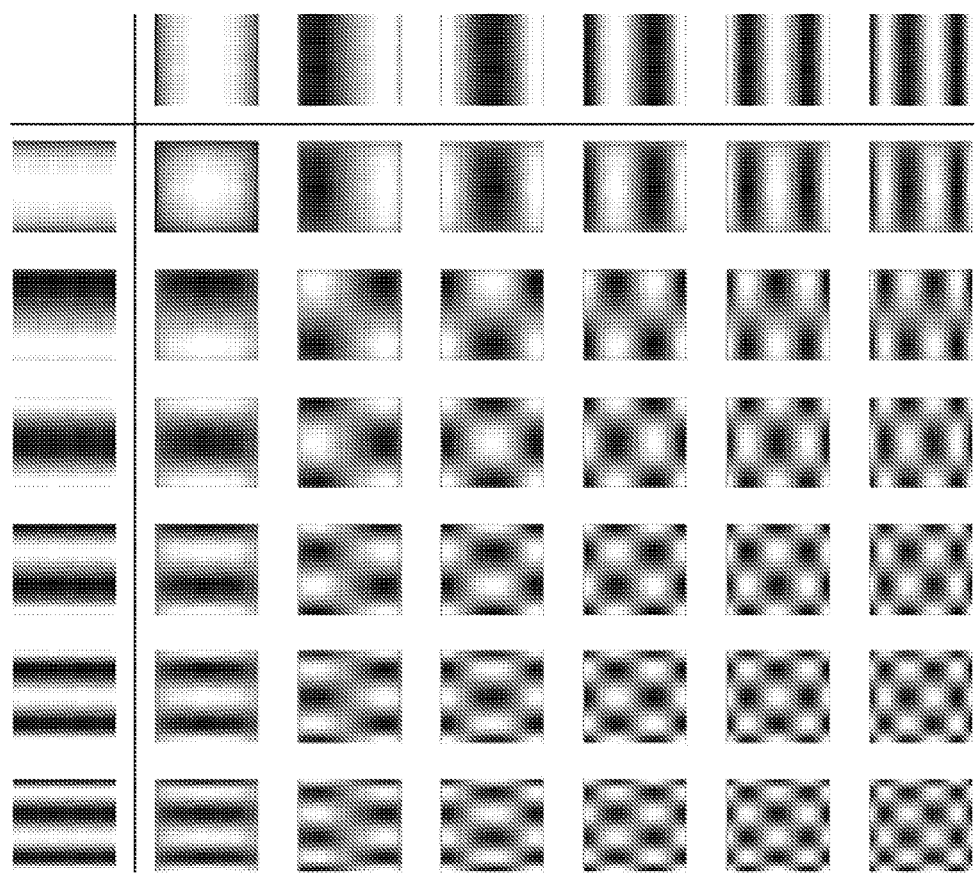
FIG. 13 shows a pictorial table of 2D Chebyshev functions.
Figure 14:
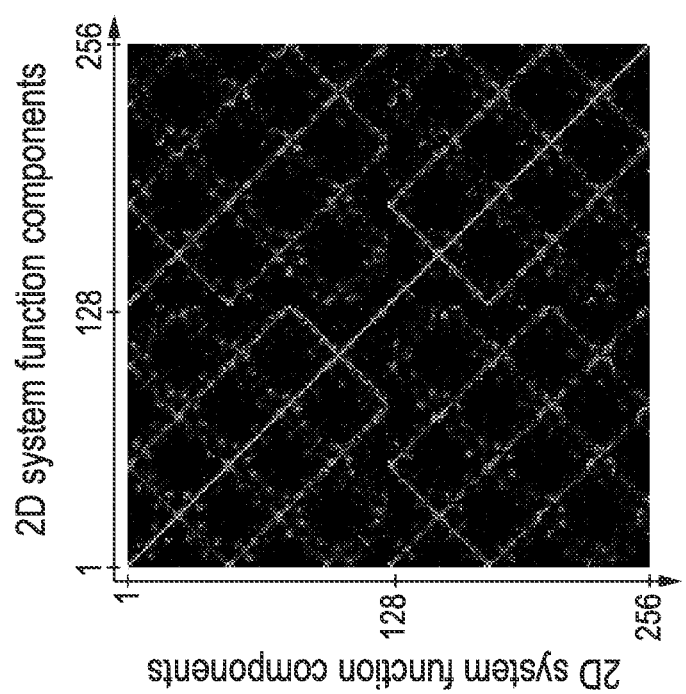
FIG. 14 shows orthogonality plots for the first 256 basis set components.
Figure 14:
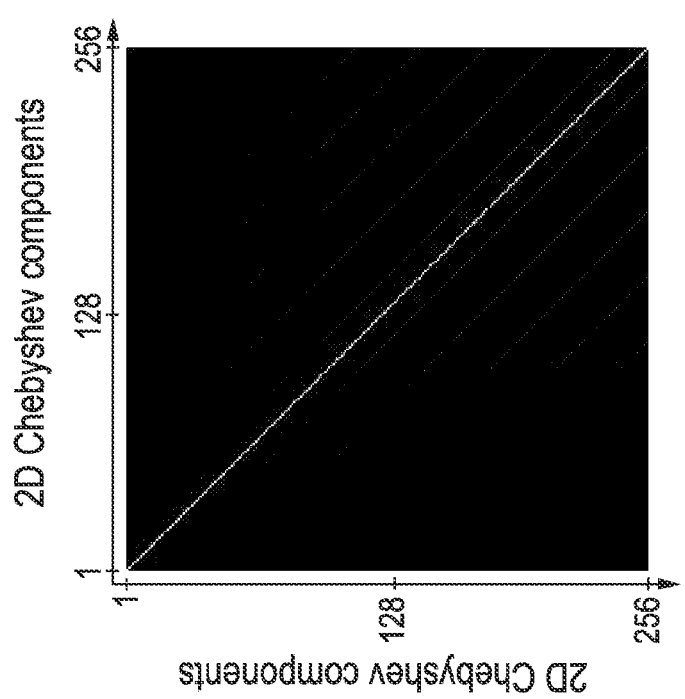

The higher the order of a system function component, the finer its spatial structure. This behavior and the general spatial patterns closely resemble 2D Chebyshev polynomials, which can be written as a tensor product of the 1D polynomials for each direction: $U_n(x) \otimes U_m(z)$. FIG. 13 plots the first components of these functions. The 2D Chebyshev functions satisfy an orthogonality relation. A graphical representation of this relation for the first 256 components is shown in the left part of FIG. 14. The inner product between orthogonal functions vanishes, so that only the product of a function with itself is non-zero, leading to the diagonal line in FIG. 14. In the right part, the corresponding plot is shown for the ideal particle 2D Lissajous system function. Bright spots and lines off the diagonal indicate that some system function components are not orthogonal with respect to each other. However, black regions prevail and one can infer that most components are orthogonal. Therefore, there is only little redundancy in the system function.

Figure 15:
FIG. 15 shows a 64×64 sample image and reconstruction from expansion into Chebyshev and system function components.

To demonstrate this, a phantom image (FIG. 15, left) is expanded into an equal number of 2D Chebyshev and Lissajous system function components, respectively. The number of components has been chosen to equal the number of pixels in the image (64×64). The image obtained from the Chebyshev transformation exhibits reduced resolution compared to the original image. The reason is that the Chebyshev functions provide higher resolution at the edges of the FOV but reduced resolution at the center. To keep the high resolution at the image center, higher Chebyshev components would have to be included in the expansion. The image obtained from the system function components has been reconstructed by inverting the system function matrix using minimal regularization to suppress noise. Half the system function components were taken from the receive x system function, the other half from the z function (as displayed in FIG. 12). Resolution of the image is better than observed for the Chebyshev expansion, but the image has small artifacts that make it appear less homogeneous. Considering the fact that some system function components are not orthogonal and therefore redundant, the image quality is quite good. The reconstructions from only the x or z components show significantly worse image quality, indicating that these subsets are not sufficient to homogeneously represent the image information.

MPI signal encoding can provide a system function that forms a well-behaved basis set capable of representing highly resolved image information.

For 1D harmonic excitation of ideal particles, the system function corresponds to a series of Chebyshev polynomials of the second kind. Therefore, a fast and exact reconstruction is provided by the Chebyshev transform.

The properties of realistic particles are introduced into the system function by a convolution-type operation leading to a blurring of the high-resolution components. This introduces a resolution limit which is determined by the steepness of the particle magnetization curve. While in principle, a higher resolution image can be regained by deconvolution, resolution provided by realistic particles without deconvolution is already high enough for many practical applications.

The system function for 2D imaging is determined by the trajectory taken by the FFP and a kernel representing the region around the FFP which contributes to the signal. The shape of this FFP kernel is determined by the topology of the selection field. The simple case of constant selection field gradients in all spatial directions has been demonstrated. For ideal particles, the kernel has sharp singularities which provide high spatial resolution. However, regions around these sharp peaks also contribute to the signal. This is probably the reason for the observation that in 2D encoding using a 2D Lissajous pattern, the system function is not exactly represented by 2D Chebyshev functions. Therefore, reconstruction cannot be done by using the Chebyshev transform as in 1D, but requires the inversion of the system function matrix. However, a close relationship between the 2D Lissajous system function and the 2D Chebyshev polynomials is obvious. This may be used to transform the system function into a sparser representation using a Chebyshev or cosine-type transformation, resulting in lower memory requirements and faster reconstruction.

The 2D Lissajous system function does not form a fully orthogonal set, since it contains redundant components. Nonetheless, it is capable of encoding highly resolved image information as shown in FIG. 10. Possible mismatches between the information content of the acquired data and the desired pixel resolution can be mediated by using regularization schemes in the reconstruction.

To speed up the tedious experimental acquisition of the system function, one can use the parity rules derived for the 2D system function. In theory, these allow to construct the complete system function from measuring only one quadrant of the rectangle of the Lissajous figure. For a 3D Lissajous figure, one octant would suffice, accelerating the system function acquisition by a factor of eight. Experimentally, the symmetry can be disturbed by non-perfect alignment of coils. Nonetheless, knowledge of the underlying theoretical functions and their parity can help to model the system function from only a few measured samples.

In a real MPI experiment, one usually acquires many more frequency components than the desired number of image pixels. Therefore, one has the freedom to make a selection of system function components to constitute a more compact basis set providing better orthogonality. For instance, duplicate system function components can be removed after acquisition to arrive at a smaller system function matrix to speed up image reconstruction. Furthermore, a selection of harmonics according to their weight can help to reduce matrix size. It is also conceivable to modify the weight of certain components to influence image resolution and SNR.

2D imaging of realistic particles has not been simulated in this work, but from the 1D derivations, one can infer that a blurring of the FFP kernel depending on the steepness of the particle magnetization curve will occur. This would remove the kernel singularities, but would also result in a slight loss of resolution, as discussed for the 1D case.

3D imaging has not been shown, but 2D results can be directly extrapolated to 3D by introducing an additional orthogonal drive field enabling 3D FFP trajectories. For a 3D Lissajous trajectory, close resemblance of the system function to third order products of Chebyshev polynomials can be expected.

The selection field topology and the FFP trajectories used in this work have been chosen for their simple experimental feasibility. However, many alternative field configurations are conceivable. For the FFP trajectory, one can as well use radial or spiral patterns, or even patterns that are tailored to the anatomy to be imaged. Trajectories can be adapted to deliver varying resolution over the image. For the selection field, a topology creating a field-free line instead of the FFP promises more efficient scanning The above shows that MPI signal encoding using harmonic drive fields in combination with constant selection field gradients provides a system function capable of representing highly resolved image information in rather compact form. The close relation to Chebyshev polynomials of the second kind can be used to speed up system function acquisition by partially modeling it, or to reduce memory requirements by applying tailored sparsity transforms resulting in faster reconstruction times.

The system functions explored here are tied to specific field configurations and scanning trajectories. Many other configurations are feasible, providing the flexibility to tailor system functions to satisfy certain experimental needs regarding speed, resolution, and sensitivity.

Some main embodiments of the method proposed according to the present invention compared to the known method shall now be illustrated by simple block diagrams illustrating the respective use of the system function (or parts thereof).

Figure 16:
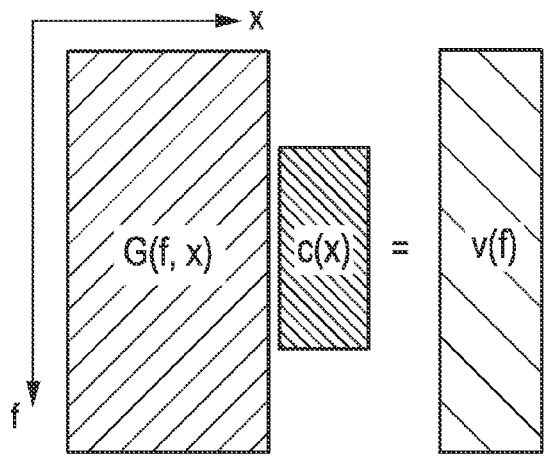
FIGS. 16-19 illustrate the use of the system function matrix or parts thereof for reconstruction according to the known method and according to embodiments of the invention.

The known method for reconstruction essentially requires the following steps (cf. FIG. 16, showing which parts of the system function are required/used):
1. Measure full "system function" once for a given combination of contrast agent, scanner geometry and trajectory:
   a. Measure time response at all spatial positions (pixels/voxels).
   b. FFT of time signal to obtain frequency spectrum at each position.
   c. Store result as matrix with frequency components (rows) versus spatial positions (columns): "system function matrix", G(f,x).
2. Measure object of interest:
   a. Acquire time response.
   b. Store Fourier-transformed response: "measurement vector", v(f).
3. Solve inverse problem G(f,x)c(x)=v(f) or a related regularized problem to obtain the concentration distribution: "image vector", c(x).

Figure 17:
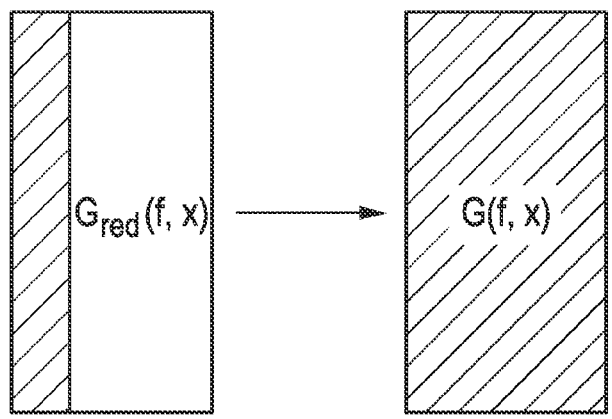
Figure 18:
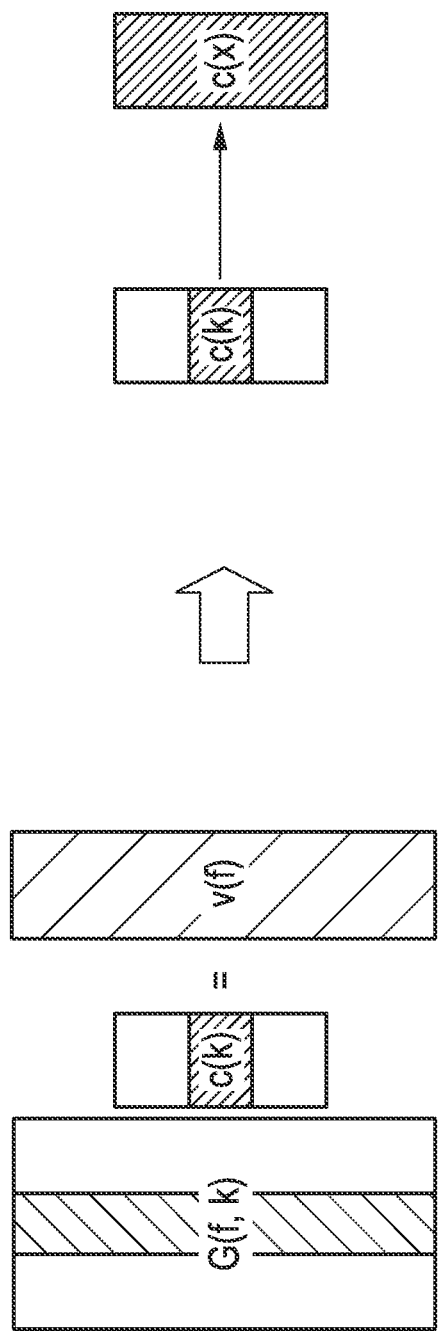

The first embodiment according to the present invention which makes use of spatial symmetries (cf. FIGS. 17, 18) essentially requires the following steps for reconstruction:
1. Using obvious mirror symmetries (cf. FIG. 17)
   a. Measure reduced system function at selected positions (e.g. one quadrant/octant or interleaved positions).
   b. Generate full system function matrix by mirror operations.
   c. Do standard reconstruction with full matrix.
2. Using a sparsity transform along the spatial directions (cf. FIG. 18)
   a. Measure system function at selected positions to obtain coefficients for the function set used to expand the spatial distribution (e.g. Chebyshev coefficients).
   b. Since the spatial distribution can be approximated by fewer components in the transform space k, the system function is represented by a sparse matrix and, if the true resolution is smaller than the voxel resolution, the spatial dimension of the vector is smaller than in real space x.
   c. Solve sparse inverse problem in transform space to obtain c(k).
   d. Use inverse transform to obtain image c(x).

Figure 19:
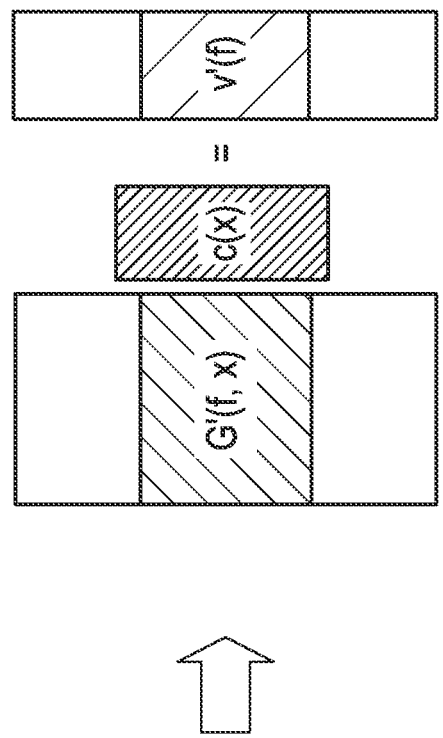
Figure 19:
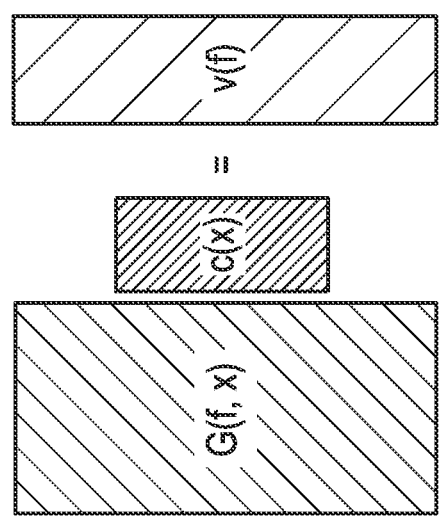

The second embodiment according to the present invention which makes use of redundant frequency components (cf. FIG. 19) essentially requires the following steps for reconstruction:

1. Take full or spatially reduced system function matrix.
2. Identify frequency components (rows) with identical spatial pattern (e.g. from theoretical considerations).
3. Sum these components in system function matrix and measurement vector.
4. Invert reduced problem to get image c(x).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An arrangement for detecting magnetic material in a region of action, the arrangement comprising:
   a selector configured to generate a magnetic selection field having a pattern in space of a strength of the magnetic selection field such that a first sub-zone having a low magnetic field strength and a second sub-zone having a higher magnetic field strength are formed in the region of action;
   a drive configured to change the position in space of the first and second sub-zones in the region of action using a magnetic drive field so that magnetization of the magnetic material changes locally;
   a receiver configured to acquire detection signals, which detection signals depend on the magnetization in the region of action, which magnetization is influenced by the change in the position in space of the first and second sub-zone;
   a storage configured to store at least a subset of a measured data set of a system function, said measured data set describing a relation between spatial position of the magnetic material and a system response for said arrangement and a trajectory along which said first sub-zone is moved for acquisition of said measured data set;
   a processor configured to
      generate a processed data set having a higher signal-to-noise ratio (SNR) than said measured data set by processing said measured data set using additional knowledge about a structure of the system function, and
      combine signals acquired at different spatial positions that share same information due to spatial symmetries existing in frequency components of the system function using additional knowledge about frequency dependent parity of the frequency components; and
   an image processor configured to reconstruct a spatial distribution of the magnetic material in the region of action from the detection signals and said processed system function data set.

2. The arrangement as claimed in claim 1, wherein said processor is configured to average the signals acquired at different spatial positions that share same information due to spatial symmetries existing in frequency components of a complete data set.

3. The arrangement as claimed in claim 1, wherein said processor is configured to reconstruct sum up frequency components of a complete data set with similar spatial information.

4. The arrangement as claimed in claim 1, wherein
   said processor is configured to acquire a complete data set of the ' system function by detecting signals while a probe of said magnetic material is subsequently placed at a plurality of different positions in said region of action, and
   said storage is configured to store the complete data set.

5. The arrangement as claimed in claim 2, wherein said processor is configured to reconstruct the complete data set from a combined signal by use of said spatial symmetries.

6. The arrangement as claimed in claim 1, wherein said processor is configured to
   reconstruct sum up frequency components of an available subset of a complete data set with similar spatial information, and
   reconstruct the complete system function from the summed up frequency components by use of said spatial information existing in the frequency components.

7. The arrangement as claimed in claim 1, wherein said processor is configured to generate the processed data set having a higher SNR than measured data set by processing said measured data set using additional knowledge about the structure of the system function.

8. A method for detecting a magnetic material in a region of action, the method comprising acts of:
   generating a magnetic selection field having a pattern in space of a strength of the magnetic selection field such that a first sub-zone having a low magnetic field strength and a second sub-zone having a higher magnetic field strength are formed in the region of action;
   changing the position in space of the two sub-zones in the region of action using a magnetic drive field so that a magnetization of the magnetic material changes locally;
   acquiring detection signals, which detection signals depend on the magnetization in the region of action, which magnetization is influenced by the change in the position in space of the first and second sub-zone;
   storing at least a subset of a measured data set of 'a system function, said data set describing the relation between spatial position of the magnetic material and the system response for said arrangement and a trajectory along which said first sub-zone is moved for acquisition of said data set;
   generating a processed data set having a higher signal-to-noise ratio (SNR)than said measured data set by processing said measured data set using additional knowledge about a structure of the system function;
   combining signals acquired at different spatial positions that share same information due to spatial symmetries existing in frequency components of the system function using additional knowledge about frequency dependent parity of the frequency components; and reconstructing a spatial distribution of the magnetic material in the region of action from the detection signals and said processed data set.

9. The method as claimed in claim 8, further comprising an act of generating the processed data set having a higher SNR than measured system function data by processing said measured data set using additional knowledge about the structure of the system function.

10. A computer readable medium comprising a non-transitory program code which when executed by a computer causing the computer to perform a method for detecting a magnetic material in a region of action, which method comprises the steps of:
generating a magnetic selection field having a pattern in space of a strength of the magnetic selection field such that a first sub-zone having a low magnetic field strength and a second sub-zone having a higher magnetic field strength are formed in the region of action;
changing the position in space of the two sub-zones in the region of action using a magnetic drive field so that the magnetization of the magnetic material changes locally;
acquiring detection signals, which detection signals depend on the magnetization in the region of action, which magnetization is influenced by the change in the position in space of the first and second sub-zone;
storing at least a subset of a measured data set of a system function, said data set describing the relation between spatial position of the magnetic material and the system response for said arrangement and a trajectory along which said first sub-zone is moved for acquisition of said data set;
generating a processed data set having a higher signal-to-noise ratio (SNR) than said measured data set by processing said measured data set using additional knowledge about the structure of the system function;
combining signals acquired at different spatial positions that share same information due to spatial symmetries existing in frequency components of the system function using additional knowledge about frequency dependent parity of the frequency components; and
reconstructing a spatial distribution of the magnetic material in the region of action from the detection signals and said processed data set.

* * * * *